(12) United States Patent
Rao et al.

(10) Patent No.: US 11,123,057 B2
(45) Date of Patent: Sep. 21, 2021

(54) FORESKIN MANIPULATOR

(71) Applicants: Rahul R. Rao, Phoenix, AZ (US); Valerie Cortez, Phoenix, AZ (US); Ahmad Basiri, Phoenix, AZ (US); Ian Conley, Phoenix, AZ (US); Lovein Thomas, Phoenix, AZ (US); Nyah Kshatriya, Phoenix, AZ (US); Zachary Fisher, Phoenix, AZ (US); Michelle Mungaray, Phoenix, AZ (US)

(72) Inventors: Rahul R. Rao, Phoenix, AZ (US); Valerie Cortez, Phoenix, AZ (US); Ahmad Basiri, Phoenix, AZ (US); Ian Conley, Phoenix, AZ (US); Lovein Thomas, Phoenix, AZ (US); Nyah Kshatriya, Phoenix, AZ (US); Zachary Fisher, Phoenix, AZ (US); Michelle Mungaray, Phoenix, AZ (US)

( * ) Notice: Subject to any disclaimer, the term of this patent is extended or adjusted under 35 U.S.C. 154(b) by 0 days.

(21) Appl. No.: 17/122,766

(22) Filed: Dec. 15, 2020

(65) Prior Publication Data

US 2021/0177392 A1    Jun. 17, 2021

Related U.S. Application Data

(60) Provisional application No. 62/948,656, filed on Dec. 16, 2019.

(51) Int. Cl.
*A61B 17/02*    (2006.01)
*A61F 6/04*    (2006.01)
*A61F 6/02*    (2006.01)
*A61B 17/00*    (2006.01)

(52) U.S. Cl.
CPC ............ *A61B 17/0218* (2013.01); *A61F 6/04* (2013.01); *A61B 2017/00477* (2013.01); *A61B 2017/00862* (2013.01); *A61F 2006/045* (2013.01)

(58) Field of Classification Search
CPC ...... A61B 17/0218; A61B 2017/00477; A61B 2017/00862; A61F 6/04; A61F 2006/045; A61F 5/41; A61F 2005/411
USPC ................................ 600/235, 238; 606/118
See application file for complete search history.

(56) References Cited

U.S. PATENT DOCUMENTS

| | | | |
|---|---|---|---|
| 2,705,951 A * | 4/1955 | Crowner | ............ A61F 6/04 128/844 |
| 3,893,455 A * | 7/1975 | McNally | ............ A61B 17/326 600/41 |
| 4,643,175 A | 2/1987 | Chapman | |
| 5,027,800 A | 7/1991 | Rowland | |
| 5,244,454 A | 9/1993 | Coates | |
| 5,269,788 A | 12/1993 | Nelson, III | |

(Continued)

*Primary Examiner* — Jessica Weiss
(74) *Attorney, Agent, or Firm* — Yakov Sidorin; Quarles & Brady LLP

(57) ABSTRACT

A device dimensioned to temporarily retract the foreskin of an uncircumcised penis to allow for the healing of an infection or disease affecting the skin of the glans of the penis, external urethral orifice and foreskin. The device may be configured to stretch and constrict as needed without creating too much pressure as to cut off circulation, and/or include non-elastic and/or elastic synthetic material. Device may be available at different sizes to the patient to ensure the best fit. Device may perform other foreskin manipulation procedures, such as pulling it forward as opposed to retracting the foreskin. The use of such device.

11 Claims, 15 Drawing Sheets

(56) References Cited

U.S. PATENT DOCUMENTS

| | | | |
|---|---|---|---|
| 5,360,390 A * | 11/1994 | Maanum | A61F 5/41 600/39 |
| 5,526,803 A | 6/1996 | Kelly | |
| 5,547,466 A | 8/1996 | McRoberts | |
| 5,728,043 A | 3/1998 | Yong | |
| 5,797,401 A | 8/1998 | Knight | |
| 5,807,299 A | 9/1998 | McRoberts | |
| 6,245,036 B1 | 6/2001 | McRoberts | |
| 6,780,194 B2 | 8/2004 | Freedman | |
| 7,377,896 B2 | 5/2008 | Dykers, Jr. | |
| 7,749,206 B2 | 7/2010 | Mayfield | |
| 7,802,577 B2 * | 9/2010 | Cvetanovic | A61F 5/41 128/845 |
| 7,972,263 B2 | 7/2011 | Runyan | |
| 8,353,918 B2 | 1/2013 | Tomlinson | |
| 8,360,957 B2 | 1/2013 | Kuri | |
| D704,330 S | 5/2014 | Cicatelli | |
| 8,808,216 B2 | 8/2014 | Diamond | |
| 8,974,471 B2 | 3/2015 | Fuerst | |
| 9,155,556 B2 | 10/2015 | Fuerst | |
| 9,204,894 B2 | 12/2015 | Jianzhong | |
| 9,289,217 B2 | 3/2016 | Fuerst | |
| 9,308,117 B2 | 4/2016 | Oh | |
| 9,345,512 B2 | 5/2016 | Altokhais | |
| 9,981,177 B2 | 5/2018 | Diamond | |
| 10,179,006 B2 | 1/2019 | Zhao | |
| 2008/0174113 A1 | 7/2008 | Brimson | |
| 2009/0158559 A1 | 6/2009 | Chardon | |
| 2009/0318754 A1 * | 12/2009 | Ettmer | A61F 5/41 600/38 |
| 2011/0146695 A1 * | 6/2011 | Taouil | A61F 5/41 128/869 |
| 2017/0348136 A1 | 12/2017 | Shaw | |
| 2019/0175383 A1 * | 6/2019 | Williams | A61F 5/37 |

* cited by examiner

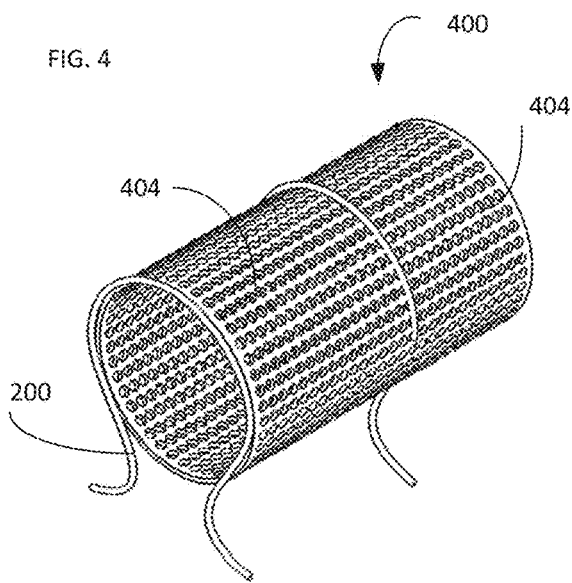
FIG. 4
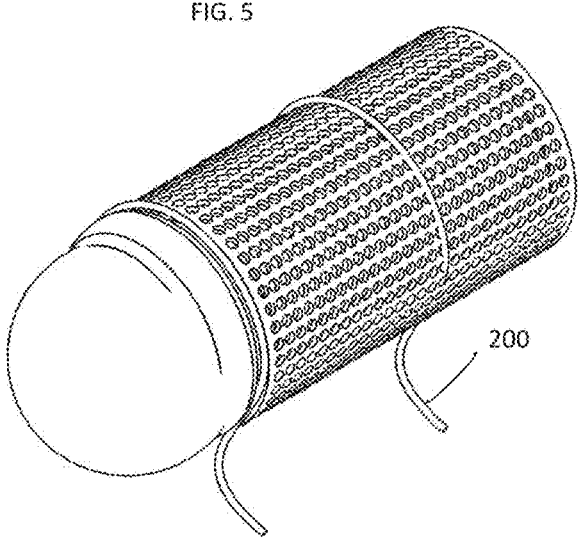
FIG. 5
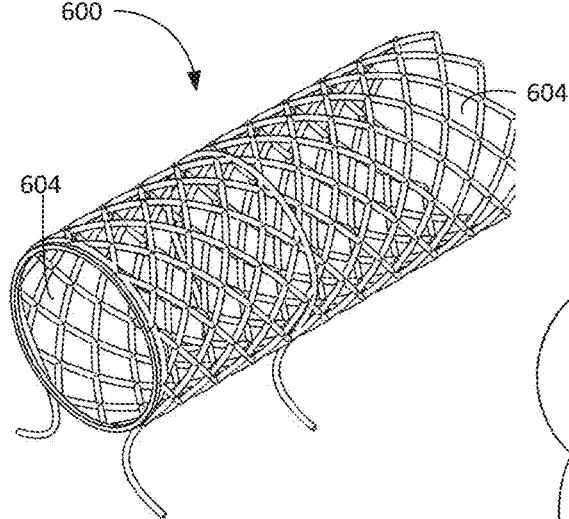
FIG. 6
FIG. 7

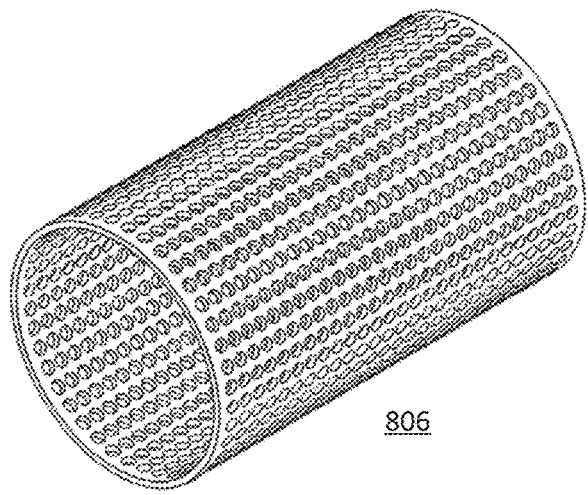
FIG. 8A
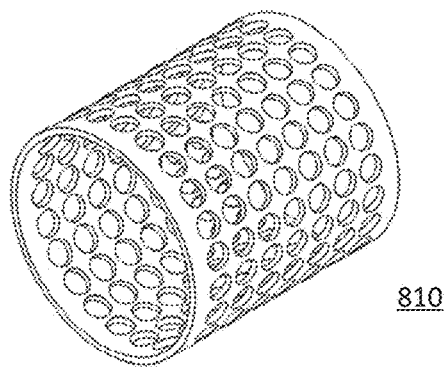
FIG. 8B
FIG. 9
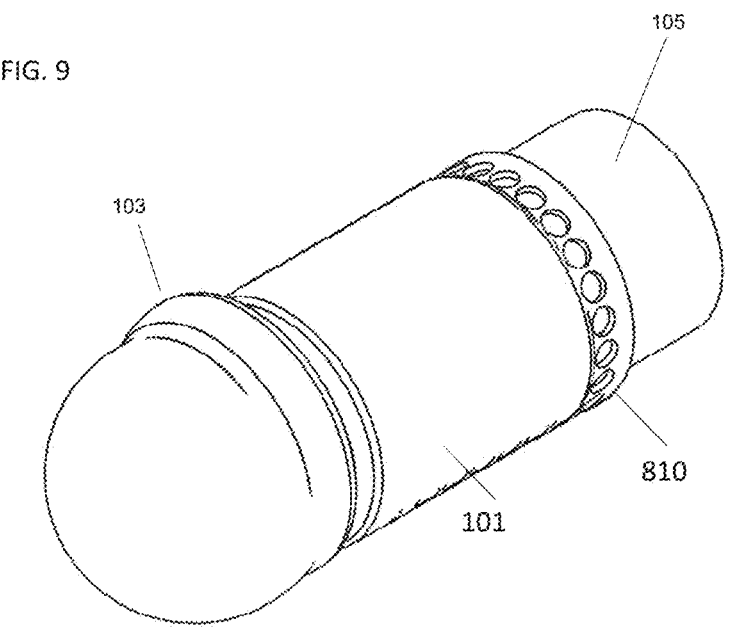

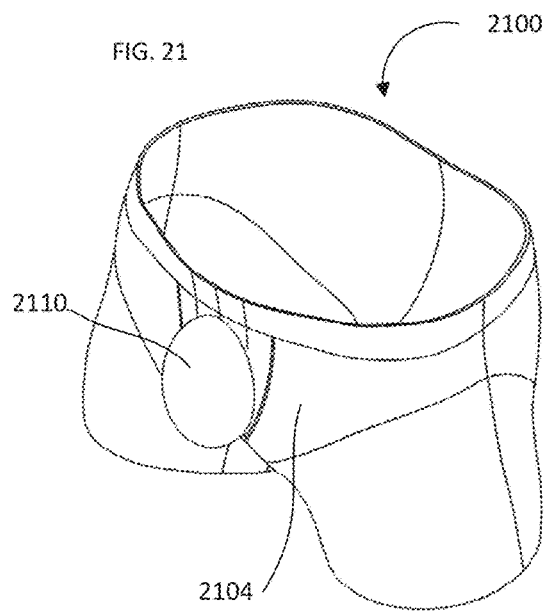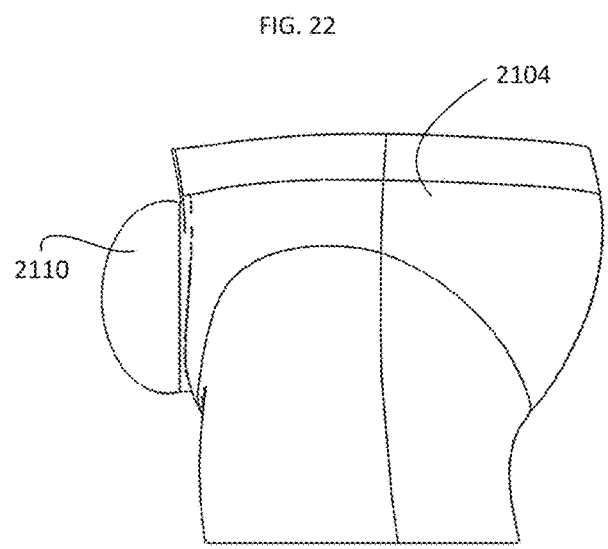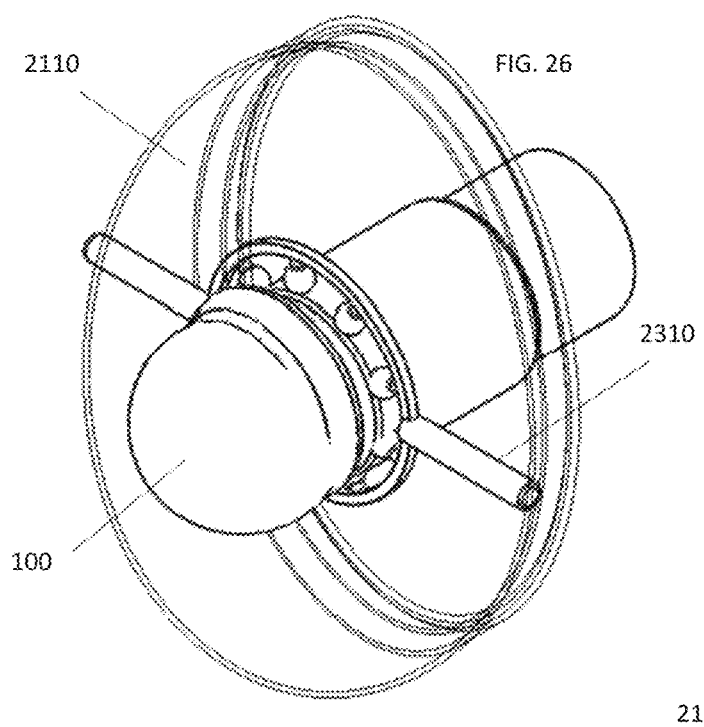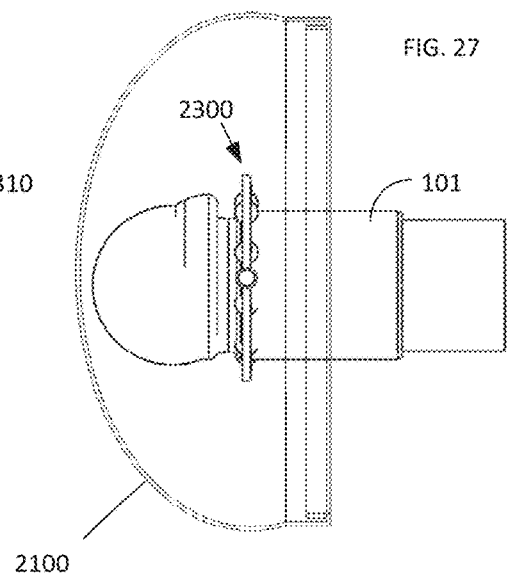

FORESKIN MANIPULATOR

CROSS-REFERENCE TO RELATED APPLICATIONS

This application claims priority from the U.S. Provisional Patent Application No. 62/948,656 filed on Dec. 16, 2019, the disclosure of which is incorporated by reference herein.

TECHNICAL FIELD

The present invention relates to a nonsurgical medical treatment for retraction and inversion of penile foreskin to expose mucosal membranes of the penis in an uncircumcised male human and devices structured to achieve this goal. More particularly, the present invention is directed to heal an infection or disease localized at/to the skin of the penis and foreskin of the penis.

RELATED ART

Among various infections that may affect the foreskin and the glans of the penis of an uncircumcised male there are Balanitis, Posthitis, Balanoposthitis, Lichen Sclerosis, Lichen Planus, Chancroids, *Candida*, Yeast Infection, Thrush, and Bacterial Infection. The most common recommended treatment for these diseases is the application of topical cream or ointment to the affected tissues including the mucosal membrane tissue of the foreskin when inverted. However, in an uncircumcised male these creams or ointments may be pushed off of the penis and foreskin by the foreskin itself in such a manner as to exit the body or by contact to surrounding clothing—this, understandably, limits the efficiency of the medical treatment. A sustained retraction of the foreskin could aid application of this topical cream and may speed up the healing process by promoting appropriate contact of the medication with the affected areas. While in severe cases circumcision may be recommended to limit the source of infection, it may not be the preferred solution for some patients who favor a nonsurgical approach. In these cases, the ability to temporarily retract the foreskin and sustain such retraction could be practically useful and equally curative.

SUMMARY OF THE INVENTION

Embodiments of the present invention provide is a penile foreskin retractor device that temporarily retracts and inverts the foreskin of an uncircumcised penis to expose the mucosal membranes and to allow for the healing of an infection or disease affecting anatomies of the penis such as the skin of the glans of the penis, external urethral orifice, and foreskin. Such diseases could include but are not limited to Balanitis, Posthitis, Balanoposthitis, Lichen Sclerosis, Lichen Planus, Chancroids, *Candida*, Yeast Infection, Thrush, and Bacterial Infection.

In one example, the penile foreskin retractor device may be configured as a stand-alone device that is attached to the exterior of the penis and foreskin that uses the glans as an anchoring feature to create a reaction force for retraction. An embodiment of the device may also be coupled with an undergarment or strap to help secure it to the body and similarly create a reaction force for retraction. In practice, the use of the penile foreskin retractor device may employ a combination of both of the above as anchors for retraction. The undergarment, when used, may be advantageously configured to have components (such as a protective cup of sorts) that serve as a protective shield for the exposed, sensitive penile skin from surrounding objects (e.g., clothing) or that are used for retracting the foreskin. The protective cup may also be used as a base for multiple retraction methods. The penile foreskin retractor device, both disposable stopper and reusable undergarment, may be made available in different sizes to the patient to ensure the best fit.

Notably, the various embodiments to be described and the components thereof are preferably designed to accommodate changing dimensions of the penis due to natural oscillation between engorged and flaccid states. Generally, embodiments of the penile foreskin retractor are dimensioned to contact the circumference of the penis and foreskin to create desired pressure to ensure a fixed position of the device on the foreskin. The device may be worn for several hours a day and can be applied and removed by the patient at any time. As discussed in more detail below, any of the components including the device and undergarment may be configured as a mesh-component based contraption to allow for grip and application of topical ointments through the mesh. (A person of ordinary skill in the art will readily appreciate that the penile foreskin retractor device should allow for the proper use of topical medication without chemical interaction or mechanical interference with the topical use on the penis and retracted and inverted foreskin.)

In at least one implementation, the penile foreskin retractor may incorporate a clip judiciously dimensioned to possess the capability to stretch and constrict the clipped member as needed to result in a desired pressure to hold the foreskin in the retracted position without interrupting blood circulation or cause discomfort while the device is worn.

When multiple clips are used, a better fit and securing of the device on the penis is afforded. For example, two clips are used to retract the foreskin. Such clips may be made with expandable and flexible material to allow comfort and circulation as the penis changes size and position during the day. One of the clips may be attached and secured to the neck of glans (behind the head of the penis) after exposing the glans. Another clip may be worn on the shaft on top of the retracted foreskin. These clips can have a geometrial shape that does not restrict the corpus spongiosum or blood circulation to enhance comfort and functionality.

The clip that is secured behind the penis glans may push the second ring toward the body using magnetic properties. The clip may be connected to another clip via solid or porous (or perforated) cylinder component or a mesh component. The first and second clips may be separated using shape-memory properties of the materials used in the mesh or the porous cylinder.

Alternatively, a hollow cylinder component or element with solid or perforated (interchangeably referred to herein as "porous") wall or a mesh component of the device may be used without a clip embedded in the device structure. The material used may have elastic properties to hold on to the penis and change geometry as the penis changes shape and size. The elasticity and pressure exerted on the penis may be able to hold the device in place and keep the skin retracted while not interfering with blood circulation or cause discomfort to the user. Generally, the penile foreskin retractor may be made out of composite materials, both by combining homogeneous materials and using multiple materials heterogeneously in tandem, to satisfy the desired application.

The cylinder element when employed maintains the retraction of the foreskin using shape-memory properties of the materials used in such cylinder element. The cylinder element (or a cylindrical component) of the device may be made of a material maintaining the permanent cylinder shape or may incorporate a flexible sheet of material, such as fabric. The permanently cylinder-shape-maintaining device may utilize a clamshell or hinge method to configure the device over the penis or the penis can be inserted in the device. The soft-sheet-based design, on the other hand, may use materials allowing bending that can then be wrapped around the penis and inverted foreskin and finally fastened to form a cylindrical shape. A fastening method such as Velcro, hook and loop, button, or similar methods can be used to hold the device in a cylindrical form and may enhance the adaptability of the device for different sizes. To further enhance adaptability of the design, an elastic material such as spandex may be introduced in whole or part with respect to the fastening method. To ensure foreskin retraction the device requires a reaction force utilizing the glans of the penis, an undergarment, or a combination of both as an anchor for retraction.

In at least one implementation, one cylinder component of the device may be complemented by another cylinder component of a different diameter (and co-axially arranged with respect to the first one) to hold the foreskin in a retracted position. The outer cylinder component is preferably in larger than the inner cylinder component not only in diameter but also in length. The use of such embodiment requires first to insert the smaller diameter cylinder component of the device over the penis; then to pull the foreskin towards the shaft to expose penis head (glans) and over the inner cylinder; and, once the foreskin is positioned over the inner cylinder, to insert the penis into the outer cylinder component until this outer cylinder reaches the neck of glans. The foreskin is then sandwiched between the outer cylinder (with a larger diameter) and the inner cylinder (with a smaller diameter). At least one of these cylinders may be made of materials that may have shape memory, magnets, or other means to create the necessary force required for sustained foreskin retraction and inversion.

One implementation of the penile foreskin retractor can utilize a spatially-tapered end to enhance the attachment of the embodiment to the penis. Alternatively, or in addition, at least one implementation may utilize synthetic finger-like protrusions to aid the device in maintaining the foreskin retraction with the use of multiple touch points instead of a circumferential surface connection, and may be added to further enhance the design while increasing comfort during use. In some embodiments of the penile foreskin retractor, the protrusions may extend from the rings or cylinders used for retraction (such as tubules, knurling, or dimples) and in other embodiments they may extend like tubules from the protective portion of an undergarment.

In one example, a pneumatic ring may be used to adjust the pressure applied on the penis to keep the retracted skin in place. Pneumatic-controlled outer circumferential cylinder for radial grip to the penis to allow the user to adjust the pressure as desired. Also, the pneumatic ring may use a self-regulating mechanism such as a balloon to allow leeway as the penis changes in size to enhance comfort and ensure the retracted foreskin remains in a retracted position. The pneumatic ring may use the undergarment as a reference point to keep the foreskin retracted and inverted.

The penile foreskin retractor may further incorporate two flexible arms attached to the undergarment that can adjust their shape to follow the changing size and shape of the penis. In this case, one side of each of the arms is attached and fixed to the undergarment, while the other side of each of the arms may be made of soft material and designed to create a smooth contact with the penis. Overall, the two arms are judiciously configured to exert pressure forces in two opposite directions (with the first art applying positive vertical force and the second arm applying negative vertical force) such that the net of the two forces substantially equals to zero.

The finger-like projection retraction arms would be placed on the opposite sides of the retracted and inverted foreskin to hold the foreskin retracted. The finger like projection retraction method may use two tubes that are crossing the sagittal plane and attached to the undergarment from both ends of the tubes. The tubes are connected to the top and the bottom of the foreskin to provide a reaction force needed for foreskin retraction and inversion.

In at least one implementation, the penile foreskin retractor may utilize multiple rings utilizing flexible polymeric materials and connected with each other along an axis of the device to create a baffle (collapsible) design. In such example, the overall shape of the penile foreskin retractor may be a conical spring. The base ring may have a bigger diameter than the ring located at the apex of the conical spring. The base ring is then positioned closer to the body of the use during the use of the device and may optionally be secured on the undergarment to hold position and the apex ring is attached to the foreskin to hold the retracted foreskin in place. The collapsible and foldable section of the baffle retraction design may allow for flexibility with the changing size of the penis. Also, the material used must provide a desired force needed for foreskin retraction and inversion.

An embodiment of the penile foreskin retractor may be used to retract the foreskin with or without manually retracting the foreskin using the fingers. In some embodiments of the device, the retracting part may retract the foreskin as the user already installed and now wears the device. In one such embodiment, the primary retraction of foreskin is achieved with the device including a cylindrical portion, a retracting ring, a handle for retraction, and a specially designed material to connect the device to the foreskin. The cylindrical portion has a slot section dimensioned to accommodate a movement of the handle and the retractable ring. The retractable handle is use to adjust the force applied to the penis, while the retractable ring may include multiple sections. In operation, the user inserts the penis into the retractable ring through the cylinder portion to expose, invert and retract the foreskin. The ring is then secured on the inverted foreskin using the radial force of the ring. This embodiment of the penile foreskin retractor allows the user to adjust retraction force as desired. The ring may use the cylinder portion as a moving rail and a locking feature. In related embodiments, the both the handle can be employed with any of the above-mentioned multiple components (including the one with a tapered end and/or multiple synthetic finger-like protrusions and/or circumferential surface connection with the penis) to enhance attachment of the device to the penis. When employed, the finger-like protrusions may be made to extend from the rings of the device used for retraction of foreskin.

BRIEF DESCRIPTIONS OF THE DRAWINGS

FIG. 1 is a schematic side view of a penis.
FIG. 2 is an isometric view of the clip shown in FIG. 3.
FIG. 3 is an isometric view of two clips retracting foreskin.
FIGS. 4, 5 provide an isometric view of an embodiment utilizing two clips connected with a perforated hollow cylinder and cooperation of such embodiment with the shaft of the penis in operation.

FIGS. 6, 7 provide an isometric view of an embodiment utilizing two clips connected with a hollow mesh cylindrical component and cooperation of such embodiment with the shaft during use.

FIGS. 8A, 8B illustrate in perspective views two generally-differently dimensioned hollow-cylindrical components of a related embodiment of the invention, which in operation are disposed co-axially with respect to one another.

FIGS. 9, 10, 11, and 12 provide schematic illustration to the process of using the embodiment that incorporates the components of FIGS. 8A and 8B.

FIGS. 13, 14 illustrate a related embodiment of the device of the invention utilizing a hollow conical component and the cooperation thereof with the shaft of the penis in use.

FIGS. 15, 16 provide illustrations of yet another embodiment that contains a hollow perforated conical component (a tapered component) juxtaposed with a hollow cylindrical unit and equipped with tactile flanges, as well as the cooperation of this embodiment with the shaft of the penis.

FIGS. 17, 18 provide perspective-view illustrations to yet another related embodiment of the device of the invention.

FIGS. 19, 20 provide an isometric view of a manual retraction device configured according to the idea of the invention, and a retracting as part of such device, respectively.

FIGS. 21, 22 illustrate an undergarment with an optional undergarment component that can be configured for use with at least some of embodiments of the invention.

FIGS. 23, 24, 25, 26, and 27 schematically illustrate yet another related embodiment of the invention (used in practice with the undergarment of FIGS. 21, 22) and employing a pneumatic ring element.

Figure 32:
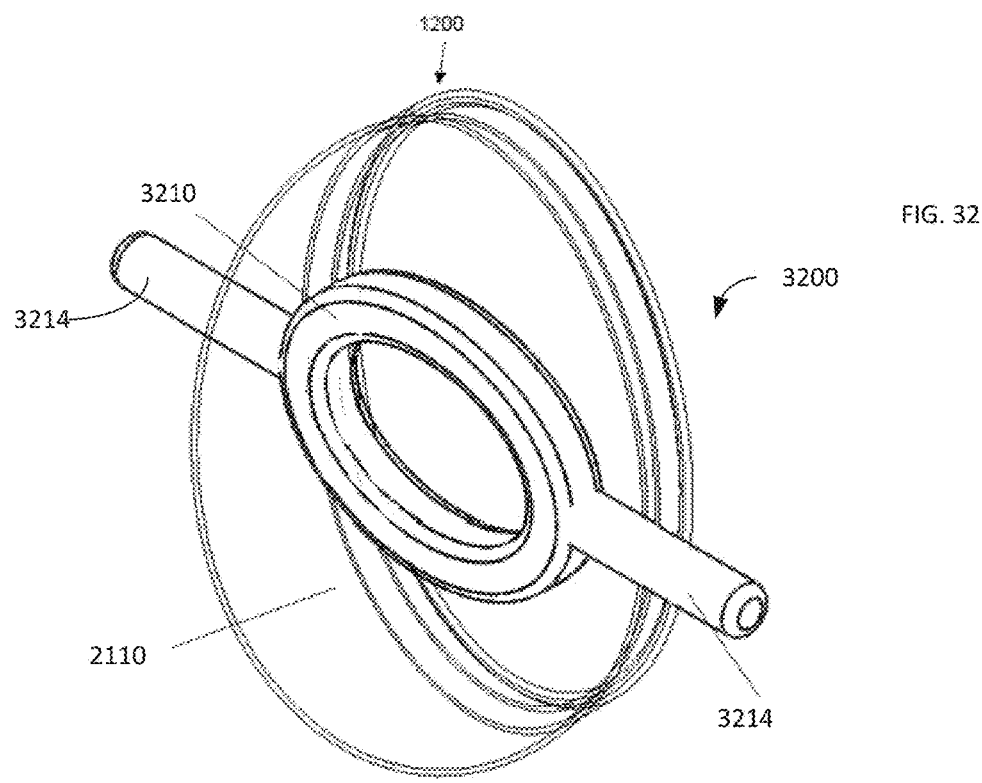
Figure 33:
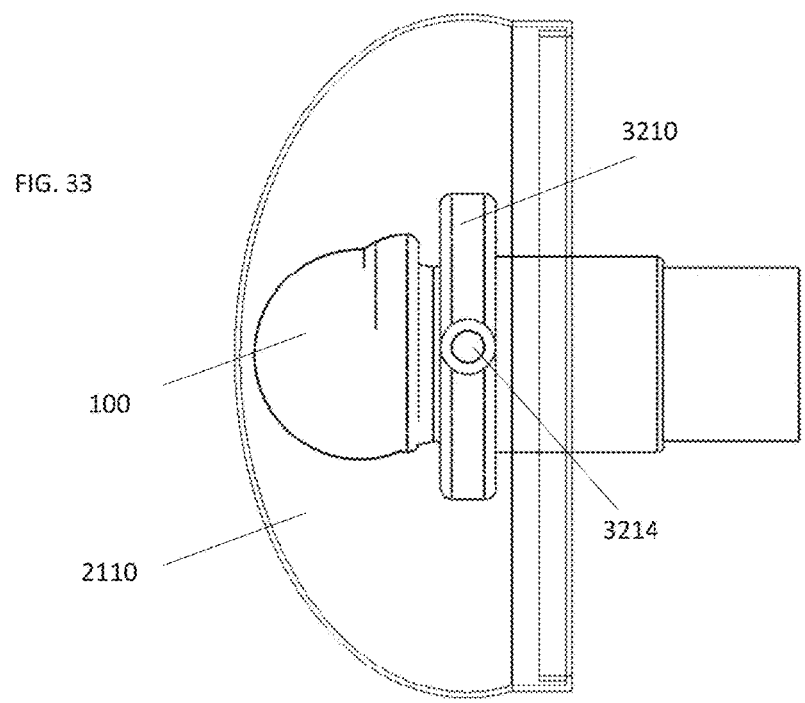

FIGS. 32, 33 schematically illustrate the structure and use of yet another related embodiment of the invention.

Figure 34A:
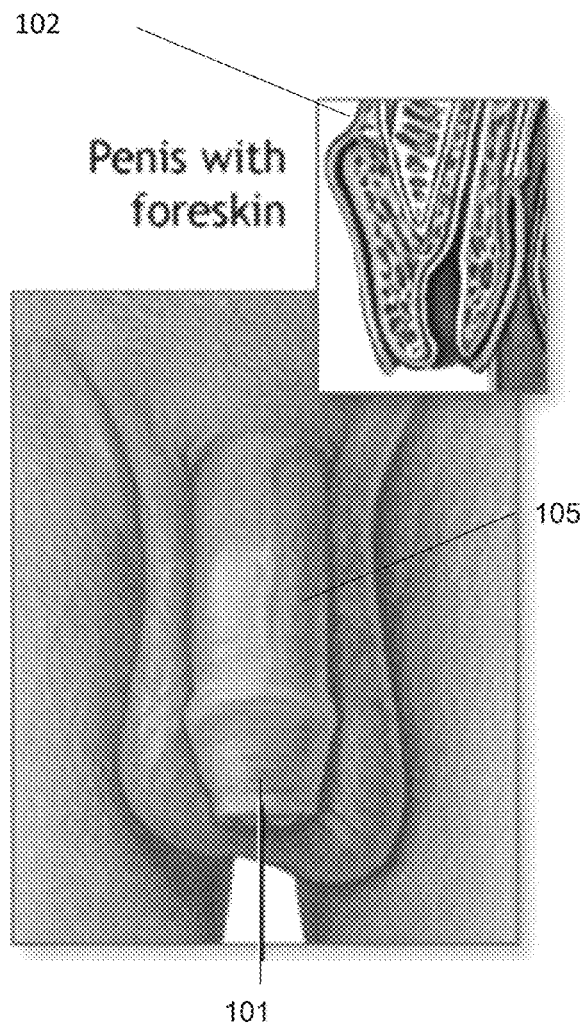
Figure 34B:
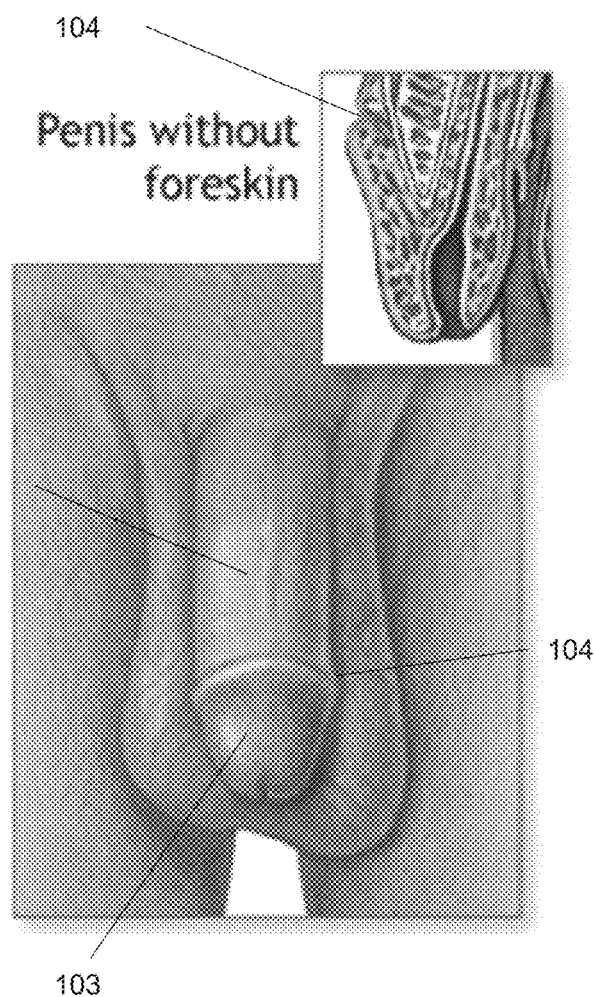

FIGS. 34A, 34B provide front views of the non-circumcised penis and circumcised penis, respectively, with identification of portions thereof relevant to the description of embodiments of the invention.

Figure 35A:
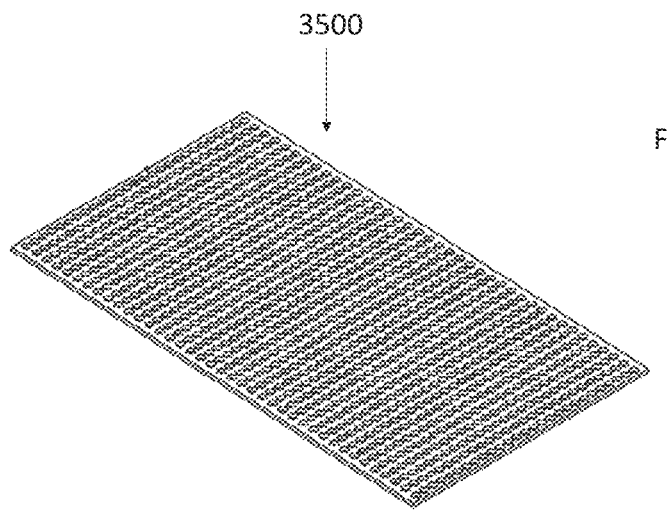
Figure 35B:
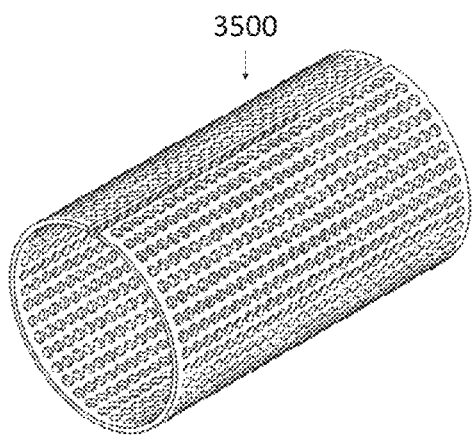
Figure 35C:
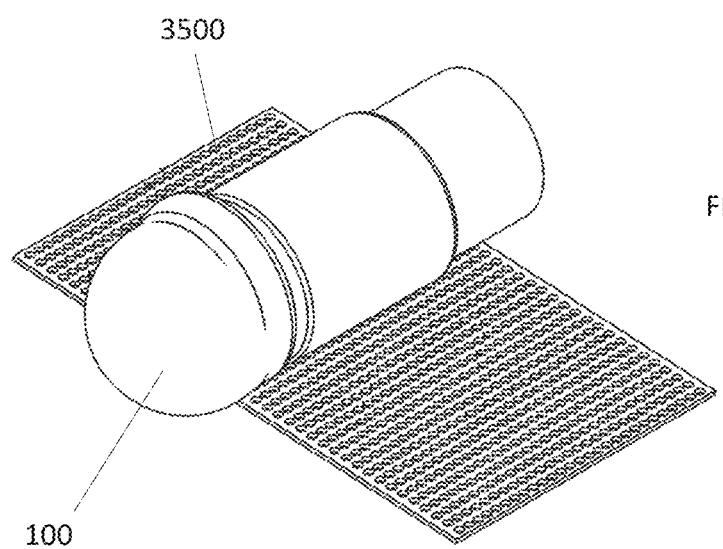

FIGS. 35A, 35B, 35C provide different views of an embodiment based on a flexible sheet fastener.

Figure 36:
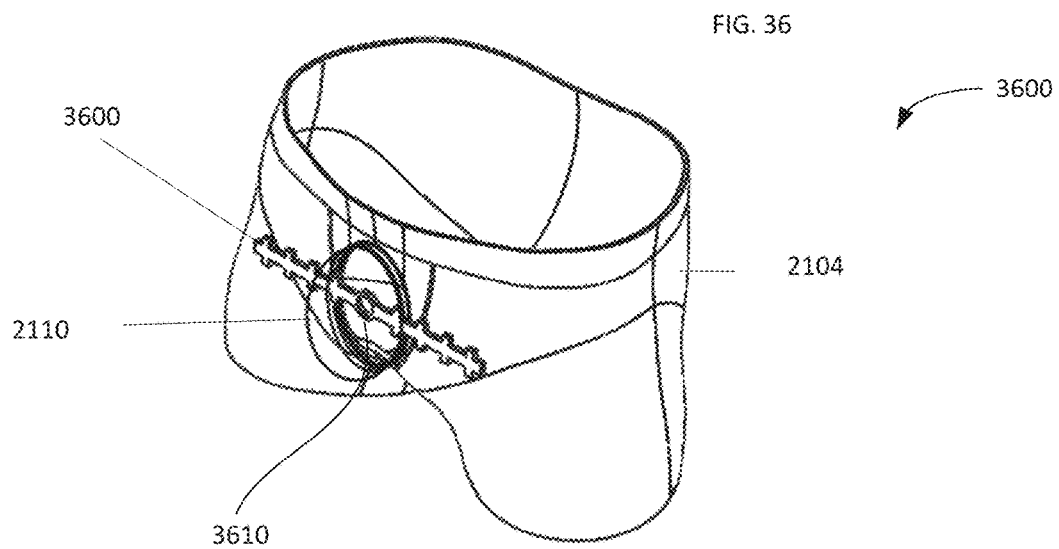
Figure 37:
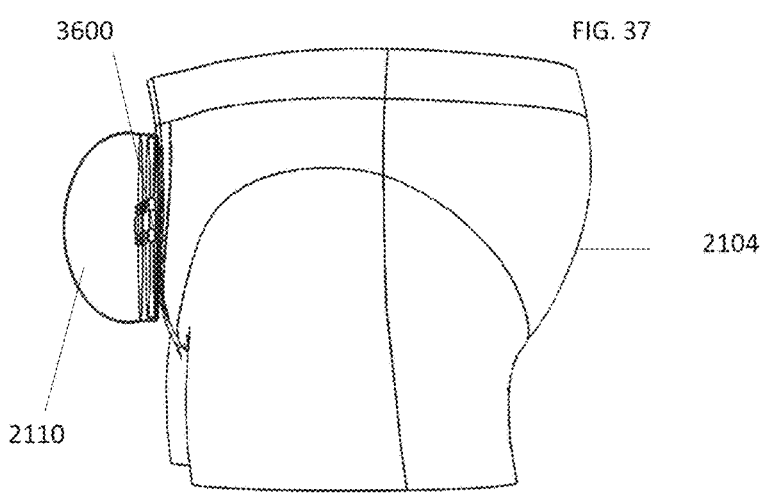
Figure 38:
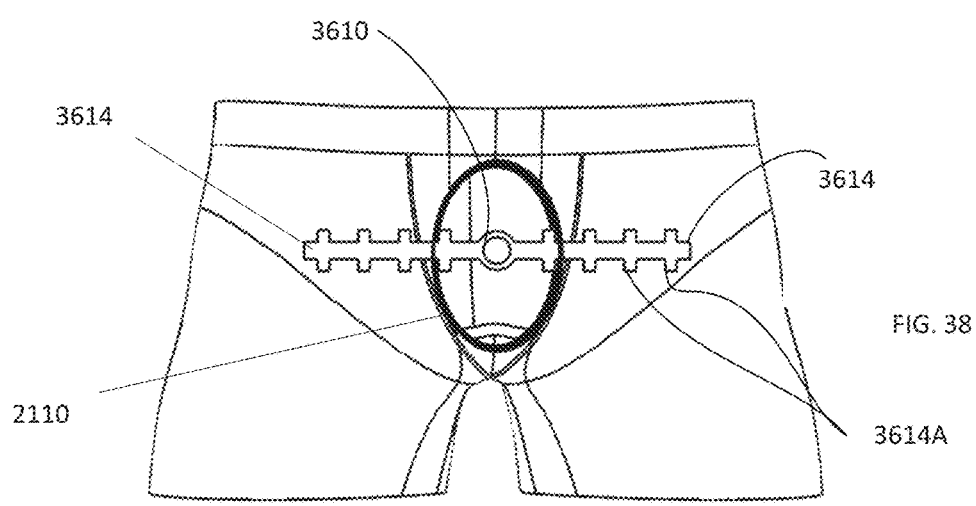

FIGS. 36, 37, and 38 illustrate schematically the structure and use of yet another related embodiment of the invention.

DETAILED DESCRIPTION OF DRAWINGS

Figure 1:
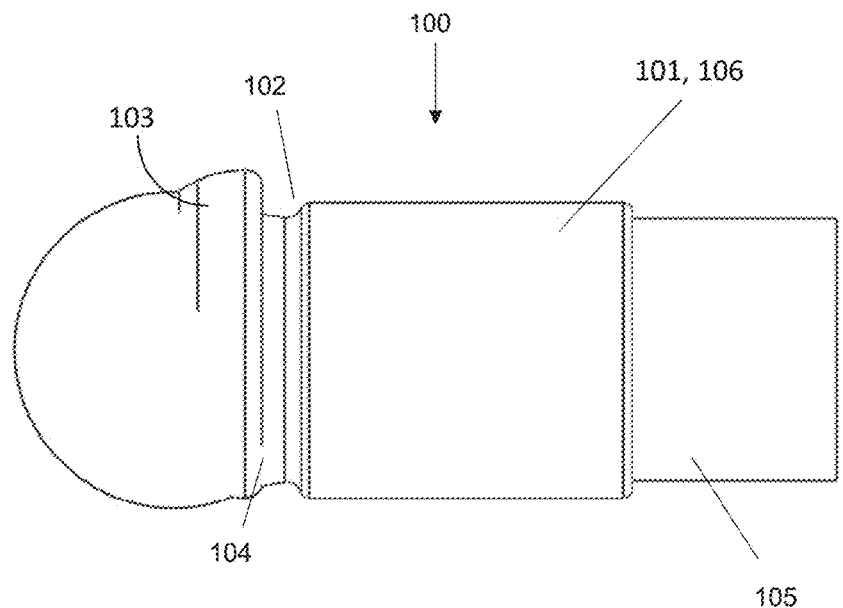

FIG. 1 schematically illustrates in a side view a model of a penis 100 used to describe embodiments of the penile foreskin retractor and to illustrate the method of wearing the penile foreskin retractor on the penis. Here, inverted foreskin in indicated as 101, the point/area of attachment of foreskin to penis as 102, 103 denotes the glans of penis with 104 identifying the neck of glans, while the penis shaft with penile skin is labeled as 105. The numeral 106 identifies the mucosal membranes on the inverted foreskin 101. See also FIGS. 34A, 34B for additional illustrations showing additional images to enhance the understanding the anatomy related to foreskin.

Figure 3:
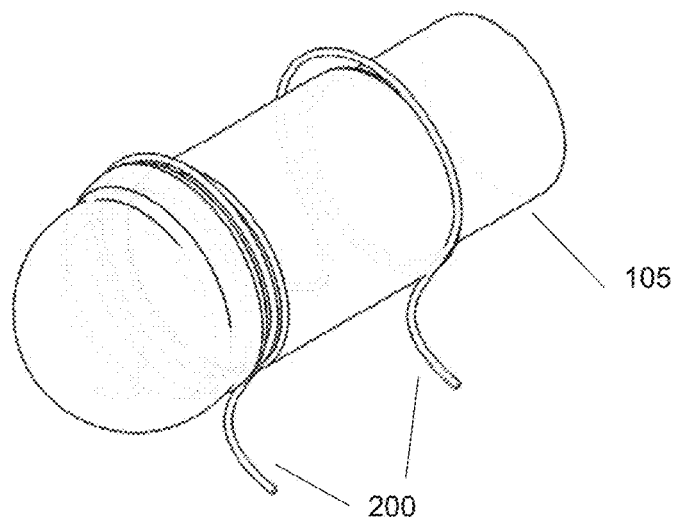
Figure 2:
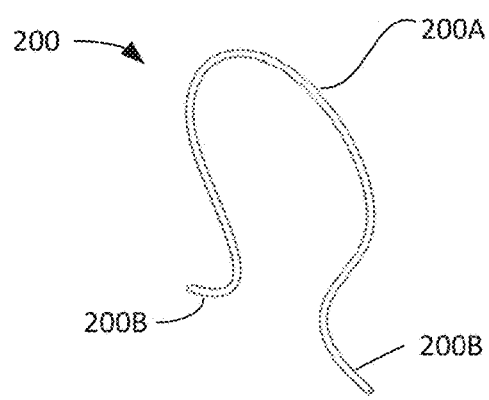
Figure 10:
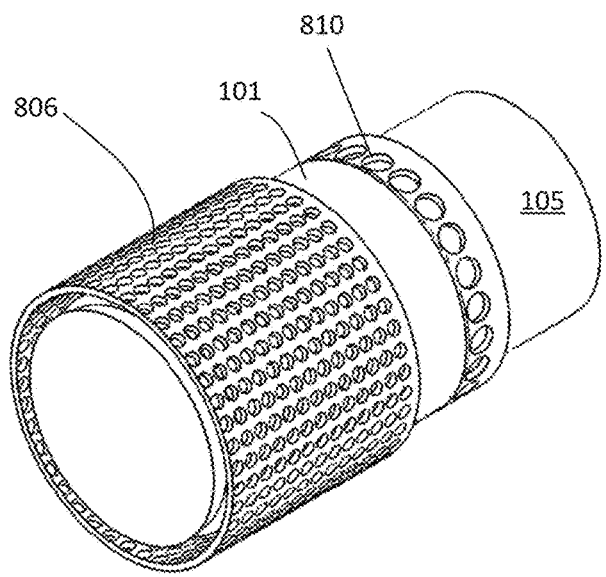
Figure 11:
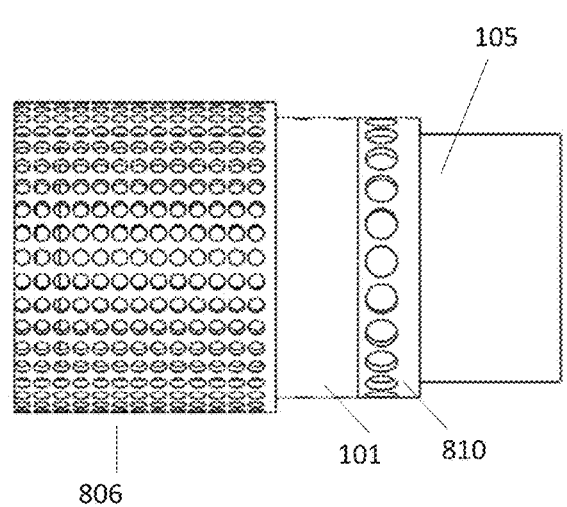
Figure 12:
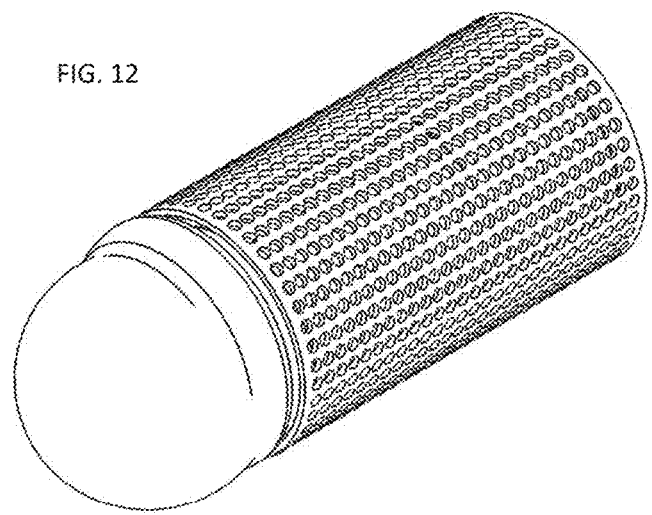

An embodiment of a clip 200 configured to retract and maintain foreskin retraction when cooperated with the penis 100 (typically, as parts of an embodiment of the overall device) is presented in an isometric view in FIG. 2. The clip is shaped as an arched coil 200A with ends 200B protruding away from the venter of the coil 200A, thereby formatting the clip 200 as (a portion of) a torsion spring. FIG. 3 illustrates a constricting (spring-like) cooperation of each of multiple clips 200 fitted with the body of the penis 100. In operation, the user manually retracts the foreskin towards the body exposing the glans 103, then securing a clip 200 to the neck of glans 104; another clip 200 may be worn on the shaft on top of the retracted foreskin, as shown in FIG. 3. The clips 200 can be appropriately configured from materials that provide magnetic repulsion of one clip from another, to maintain a desired distance between the clips disposed apart from one another, to maintain a desired distance therebetween and therefore maintaining the retraction of the foreskin. In such a case, the front clip that is secured immediately behind the penis glans 103 may push the second ring toward the body using magnetic repulsion forces.

In a related implementation, multiple clips 200 are used not by themselves but in cooperation with a tube-like and generally cylindrical element shown in the specific embodiment of FIGS. 4, 5 as a porous or perforated hollow cylinder 400 (or a hollow cylinder the wall of which contains multiple openings 404 therethrough, optionally both along the length of the cylinder 400, arranged in multiple columns, and circumferentially, arranged in multiple rows). In one case, the openings 404 are formed by appropriately perforating the sheet of material forming the wall of the cylinder 400. Depending on a particular implementation, the aggregate area defined by the openings 404 is at least 30% or more, 50% or more, or even 70% or more of an area of the outer surface of the wall of the cylinder 400. Notably, the areal density of the holes/openings 404 may be higher on that portion of the cylinder that retracts and overlaps the retracted foreskin (that is, in the portion of the cylindrical element 400 that in operation is installed proximal to the body of the user). In one implementation, at least one of the multiple clip 200 (as shown—the one positioned distally with respect to the glans 103) is cooperated with the embodiment 400 by passing the ends 200B of the clip through two corresponding throughout openings 404 that are approximately opposing one another. In a related implementation (not shown), at least one of the multiple clips is disposed above and around the cylinder 404.

In operation, the user pulls the foreskin towards the shaft to expose penis head (glans) 103 and then inserts the penis into a proximal clip 200 cooperated with the cylinder 400 and through the 201, see FIG. 5. Furthermore, the user may also pull the porous/perforated hollow cylinder 404 closer to the body until the edge of the cylinder is aligned with the neck of glans 104 (behind the head of the penis). Therefore, another (front) clip 200 is secured on the penis neck spring action of the clip and prevents the cylinder 404 from sliding towards and onto the penis glans 103 thereby keeps the retracted foreskin in place on the shaft of the penis under the cylinder 400 and away from the penis head; FIG. 5.

When none of the clips 200 is embedded into or passed through the structure of the cylinder 400, the position first and second clips 200 (with respect to the body of the cylinder 400) may utilize shape-memory properties of the materials used in the porous cylinder.

In this case, the used material may be chosen (such as nitinol (nickel-titanium), PTFE, Spandex, Silicone, Polyurethane, to name just a few) to have appropriate elastic properties to hold on to the penis and change the geometry of the cylinder (diameter, length) as the penis changes its shape and size. The elasticity and pressure exerted on the penis by such porous cylinder portion holds the device in place and keep the skin retracted while not interfering with blood circulation or cause discomfort to the user.

In an embodiment 600 of FIGS. 6, 7 (which is related to the embodiment 400), the cylindrical portion is shown formed from a mesh or netted material with multiple mesh openings 604.

In reference to FIGS. 8, 9, 10, 11, 12, an embodiment utilizing a cylindrical element (such as a porous cylinder 400, or a mesh cylinder 600) may employ multiple of such cylindrical elements of different diameters cooperated coaxially with one another. Here, the cylinder 806 of FIG. 8A is larger both in diameter and in length as compared to the cylinder 810 of FIG. 8B. The method of foreskin retraction utilizing the embodiment employing both cylinders requires the user first to insert the smaller diameter cylinder 810 over the penis. The user then pulls the foreskin 101 towards the shaft to expose penis head (glans) 103 and over the cylinder 810, as is schematically illustrated in FIG. 9. Once the foreskin is positioned over the cylinder 810, the penis is inserted into the cylinder 806 until it reaches the neck of glans 104 (see sequence of FIGS. 10, 11, 12), thereby sandwiching the foreskin 101 between the cylinders 810 and 806. The cylinders 806, 810 may be made of materials that may have shape memory properties, magnetic elements, or other means to create the necessary force required for sustained foreskin retraction and inversion. As shown, the edge of the device may abut to the glans 103 of the penis to create a reaction force needed for the foreskin retraction and inversion.

Figure 13:
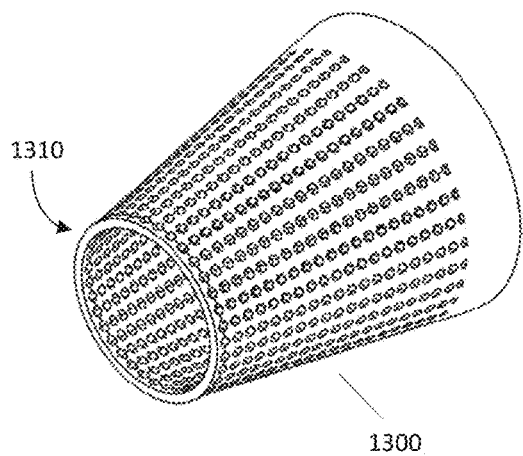
Figure 14:
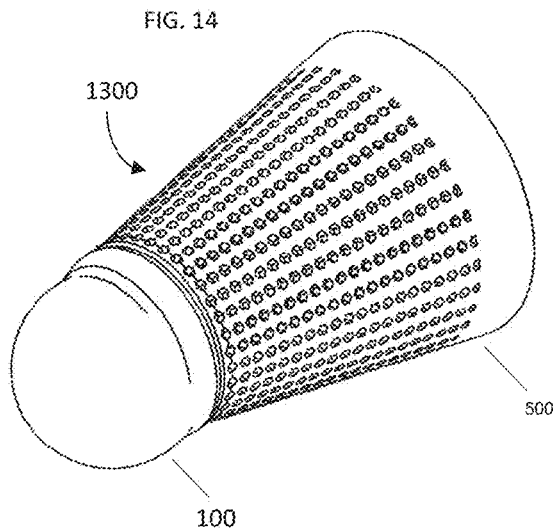

In at least one case at least one of the cylindrical components (e.g., 400, 600, 806 etc) may be spatially-tapered—as schematically illustrated in the case of embodiment 1300 of FIGS. 13, 14—to form a substantially-conical component the front (narrow) end 1310 of which is in practice disposed to abut the glans 103 to enhance the attachment to the penis.

Figure 15:
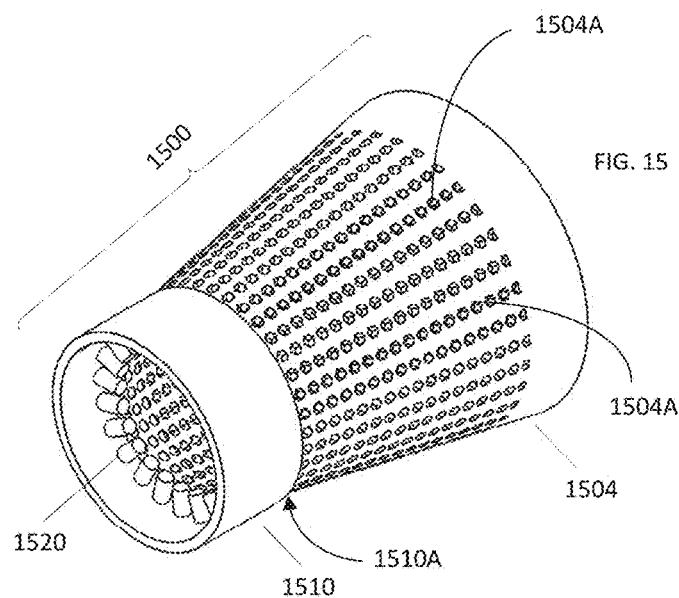
Figure 16:
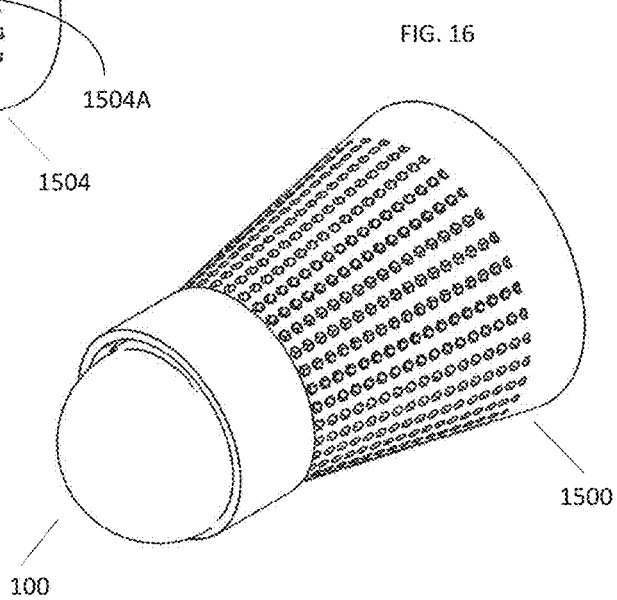

Alternatively or in addition, either the cylindrical or the conical component of the device (whether it is formatted as a "porous" component that contains a multiplicity of throughout openings, or a substantially spatially-uninterrupted wall, or a wall made of a mesh) may be complemented with finger-like protrusions disposed on the inner side of the corresponding cylinder (or cone) to aid the action of retracting the foreskin by providing multiple touch points instead of a circumferential edge or surface contact between the cylindrical (or conical) component of the device and the foreskin while, at the same time, increasing comfort of the wearer during the use of the device. As shown in FIGS. 15, 16, for example, the embodiment 1500 includes a substantially conical element 1504 containing multiple throughout openings or "pours" 1504A and providing a taper from the first end of it (disposed in operation closer to the body of the user) to the second or front end of it (disposed in operation at the glans 103) and the spatially-uninterrupted cylindrical component or ring 1510. For the convenience and comfort of use of the device, the diameter of the cylindrical component 1510 and that of the front end of the conical porous component 1504 are substantially equal to one another, such that the components 1504, 1510 are merging one into another along the edge of the cylinder 1510. In one implementation, such merging is structured to be tangential to ensure that at least one of the outer and inner surfaces of the embodiment 1500 in the immediate vicinity of the edge 1510A is differentiable. As is schematically illustrated in FIG. 15, on the inner surface of the embodiment 1500 the multiplicity of finger-like protrusions 1520 (formed in one case from polymeric material) are disposed in a circumferential manner around the line of the edge 1510A. As illustrated in FIG. 16, the ring element 1510 of the embodiment 1500, when positioned over the penis, may be at least partially covering the glans 103. Understandably, any of the previously-discussed implementations in which a cylindrical component is used (e.g., 600) can also be complemented with the protrusions similar to protrusions 1520—in this case, the protrusions may be formed on the inner surface of the corresponding cylinder substantially close to or at the edge of it. As a non-limiting example, finger-like protrusion geometry may be cylindrical, conical, knurled, and/or dimpled. Lengths of these protrusions may be from about 1 mm to about 15 mm. Thickness or diameter may be in the range of 1 mm to 10 mm. Number of protrusions will depend on the diameter of the component 1510A, but separations of protrusions along the circumference is preferably equidistant and approximately equal to half the diameter of a protrusion. The practical reason for this formulaic distribution of protrusions is to grip the foreskin and create an inversion of the foreskin as the penis is introduced through the device. Protrusions will then act as the stopper elements to hold inverted foreskin in place.

Figure 17:
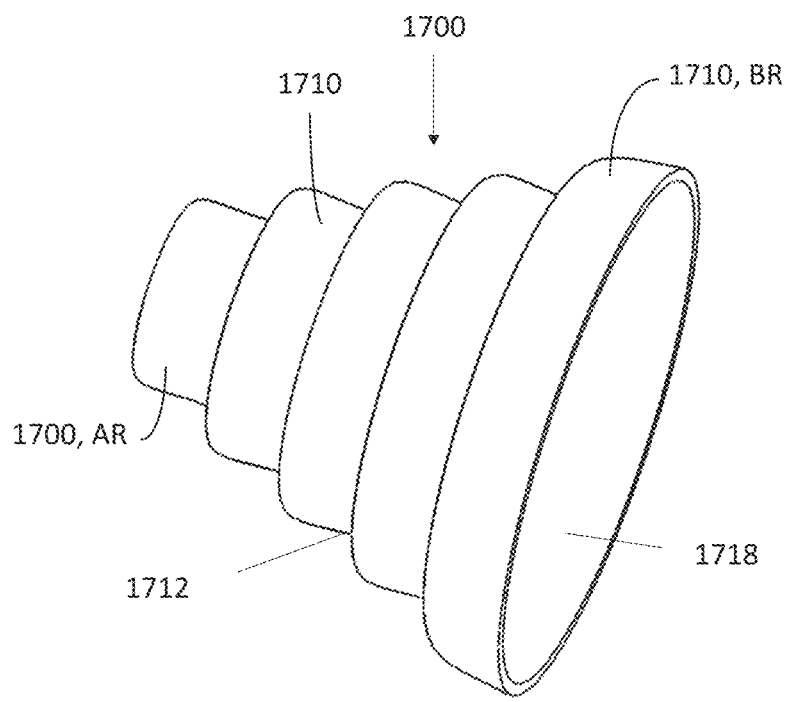
Figure 18:
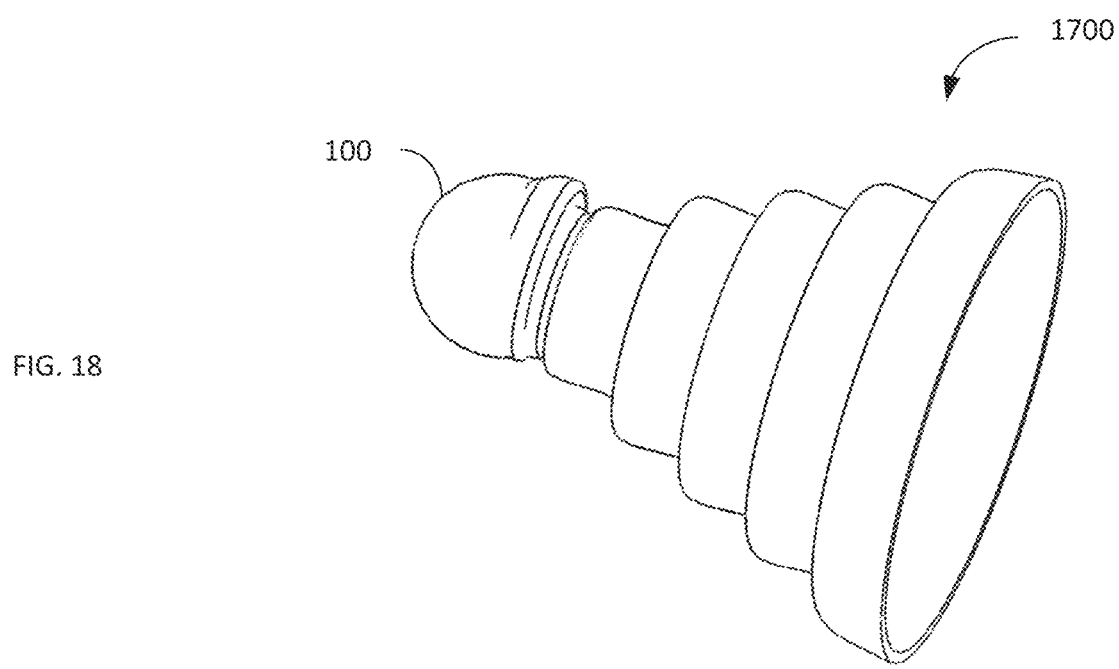

Referring now to FIGS. 17, 18, in at least one embodiment 1700, the retraction device of the invention may be configured as a baffled hollow device—the one employing multiple rigid ring-like hollow elements 1710 of different diameters connected with each other using connecting sections 1712 made of flexible polymers material(s). The device's overall shape in this case may be a conical spring with the base ring BR in operation positioned closer to the body of the wearer. In this case, understandably, the base ring BR is dimensioned to have a bigger diameter than the immediately-neighboring ring, and the diameters of the remaining rings 1710 are reduced with the apex ring AR having the smallest diameter of them all. Due to the presence of the flexible connecting sections 1712, the device 1700 is collapsible upon itself, such that is a "folded" or "collapsed" state at least one of the rings 1710 having a smaller diameter is positioned inside the ring 1710 that has a larger diameter. The collapsible and foldable section of the baffled retraction device 1700 may allow the device to move with the changing size and shape of the penis with a desired force of retraction to provide a reaction force needed for foreskin retraction and inversion. To install the device, the user pulls the foreskin towards the shaft to expose penis head (glans) 103 and then inserts the penis into baffled retraction device 1700 from the base ring BR (as shown by numeral 1718) toward the apex ring AR. The base ring BR may then be secured on the undergarment (as discussed in more detail below) to hold position while the apex ring remains in contact with the foreskin to hold the retracted foreskin in place as shown in FIG. 18.

Figures 19, 20:
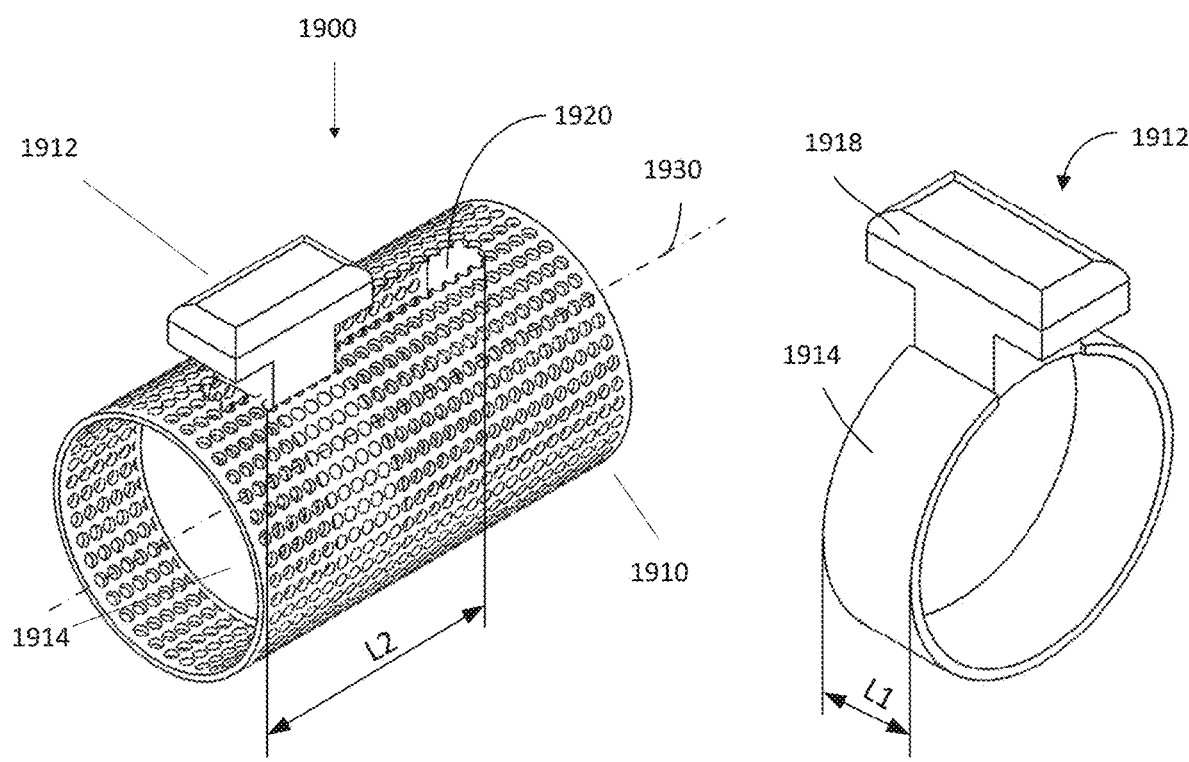
Figure 23:
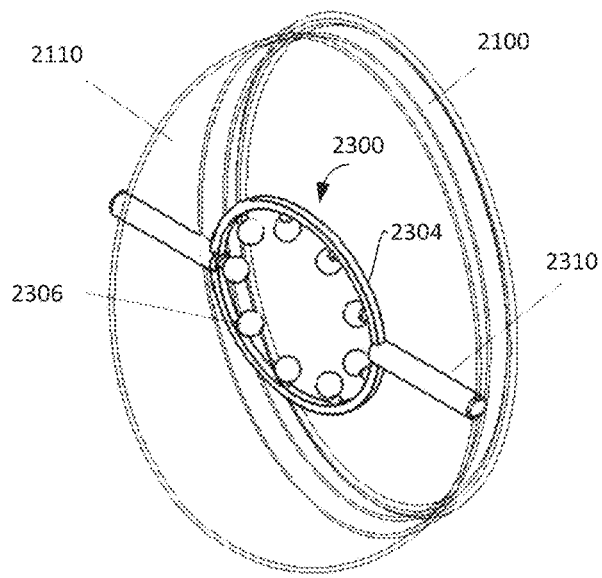
Figure 24:
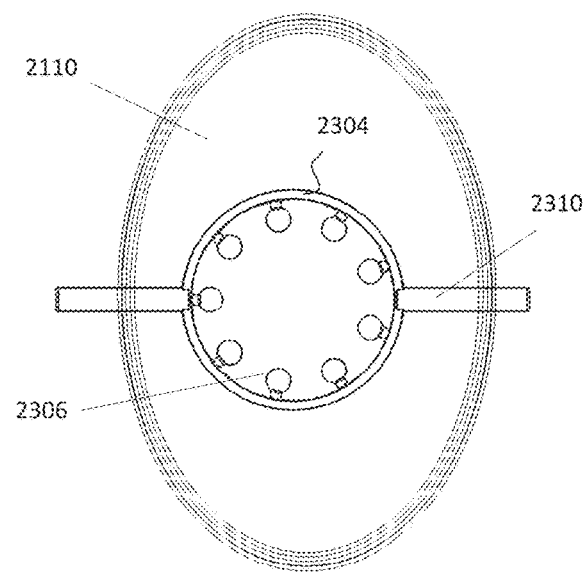
Figure 25:
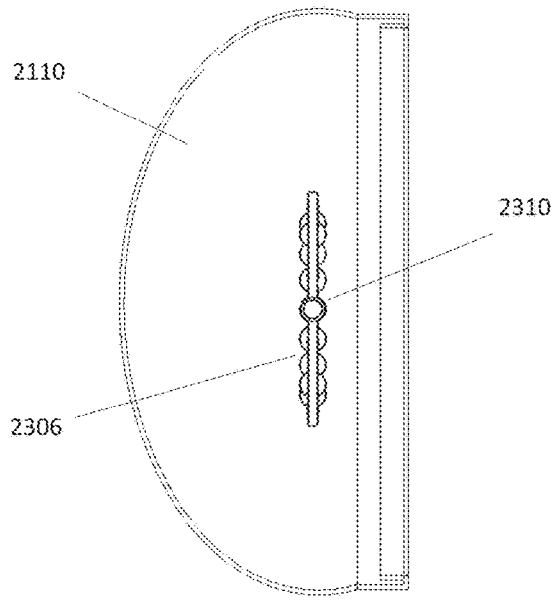

In yet another related embodiment, the embodiment 1900 of the foreskin retraction device includes a cylindrical component 1910 (shown in FIG. 19 to be of a porous variety that is juxtaposed with a retractor unit 1912. The retractor unit 1912 contains a ring 1914 equipped with a handle or button 1918. When assembled together, the ring 1914 of length or width L1 is disposed inside of and substantially coaxially with the cylindrical component 1910 while the neck of the handle 1914 is passed through a slot or throughout groove 1920 (formed in the body of the cylindrical component 1910 and shown in FIG. 19 to have a length L2>L1). The geometries of the components 1910, 1914 are judiciously chosen to ensure that the ring 1914 smoothly slides inside the cylinder 1910 in contact with the inner surface of the cylinder 1910 and without mechanical rattling when the handle 1918 is moved along the slot 1920. The material of the ring 1914 is chosen to maintain connection with the foreskin and apply such desired force.

In operation, the device 1900 is disposed around the penis with the ring 1914 abutting the glans 103 and the handle 1914 in close proximity to the glans. In particular, the user pulls the foreskin towards the shaft to expose penis head (glans) 103 and then inserts the penis into the retracting ring 1914 through the cylinder 1910. The user may also pull the cylinder 1910 until it reaches the neck of glans 103 (behind the head of the penis). The ring 1914 is then secured on inverted foreskin using ring elasticity. The design allows the user to adjust retraction force as desired: the retractive handle 1918 is configured to allow the user to adjust the force when moving the ring 1912 backwards to create a force required for skin retraction and inversion. The ring 1914 may be use the cylinder 1910 as a moving rail and a locking feature. In some embodiments of the device, the retracting part 1912 may retract the foreskin as the user wears the device and in other embodiments. The user must retract the foreskin manually before wearing the device. (Additionally, as discussed below, the embodiment 1900 may be anchored to accessories worn around the body such as an undergarment to provide a reaction force needed for foreskin retraction and inversion.)

Substantially any embodiment of the retraction device may be in practice anchored to accessories 2100 shown in FIGS. 21, 22 worn around the body of the user (such as an undergarment 2104) to provide a reaction force needed for foreskin retraction and inversion. The undergarment shown in FIGS. 21, 22, may also have judiciously dimensioned constituent component(s)—for example, a component 2110 (shown to be similar to an athletic cup, or alternatively a baffled retraction device 1700 already discussed above) configured to serve as a protective shield for the exposed, sensitive penile skin from surrounding objects (e.g. clothing) and/or to be used simultaneously for retracting the foreskin. When the constituent component 2110 is configured as a protective cup, it may also be used as a base or support for multiple foreskin-retraction methods.

Furthermore, auxiliary units may be used to either be operated independently to retract and invert the foreskin or complement another embodiment of the retractive device. For example, as schematically illustrated in FIGS. 23, 24, 25, 26, and 27 the pneumatic ring-based device 2300 may be used to adjust the pressure applied on the penis to keep the retracted skin in place. The pneumatically-controlled outer circumferential cylinder or ring-like element 2304 for radial grip to the penis allows the user to adjust the pressure as desired, while the rod-like or tubular arms 2310 extending from the ring 2304 may in operation be affixed in/juxtaposed with at least one opening (not shown) formed in a protective cup 2110, for example. In one specific implementation, the pneumatic ring 2304 may use a self-regulating mechanism such as at least one radially-pointing extensions dimensioned as finger-like protrusions (configured, for example, as balloons or spheroids) 2306 on an inner surface of the element 2304 to allow a leeway as the penis changes in size to thereby enhance comfort and ensure retracted foreskin remains in retracted position. The user pulls the foreskin towards the shaft to expose penis head (glans) 103, then inserts the penis into pneumatic ring device 2300 until reaches the neck of glans 103 or the inverted foreskin. Then the device 2300 is secured in place with the use of the accessories 2100 (and optionally within the protection element 2110), as shown in FIGS. 26, 27 (here, the openings in the element 2110 through which supporting the arms 2310 are pulled are not shown for simplicity of illustration).

Figure 28:
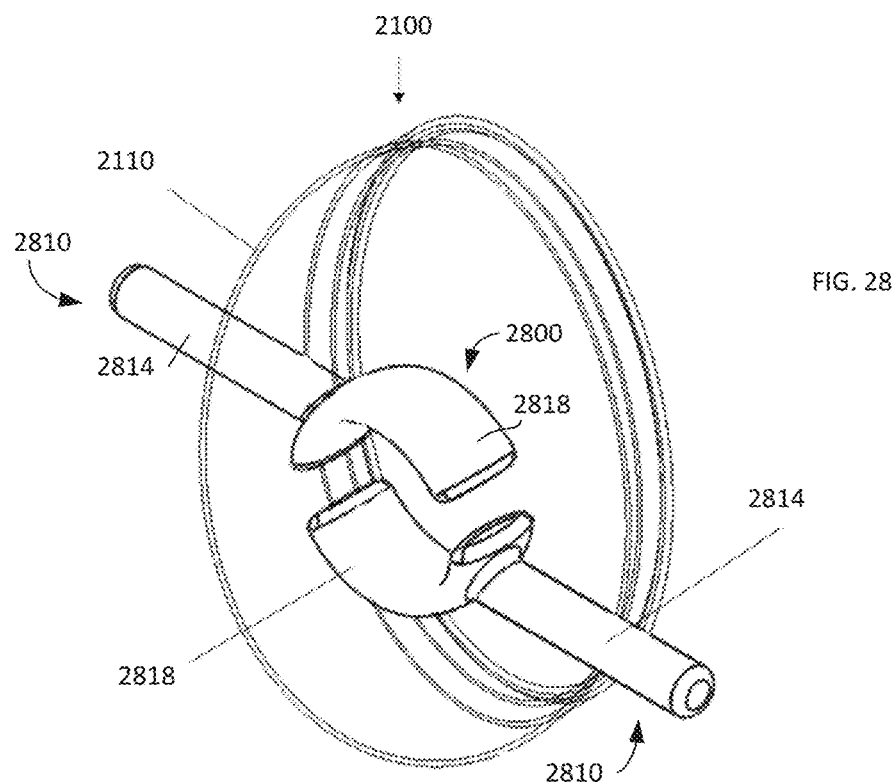
FIGS. 28, 29 illustrate in isometric view a finger-like projection retraction embodiment of the device mounted in the protective cup of the undergarment, by itself and mounted on the shaft of the penis, respectively.
Figure 29:
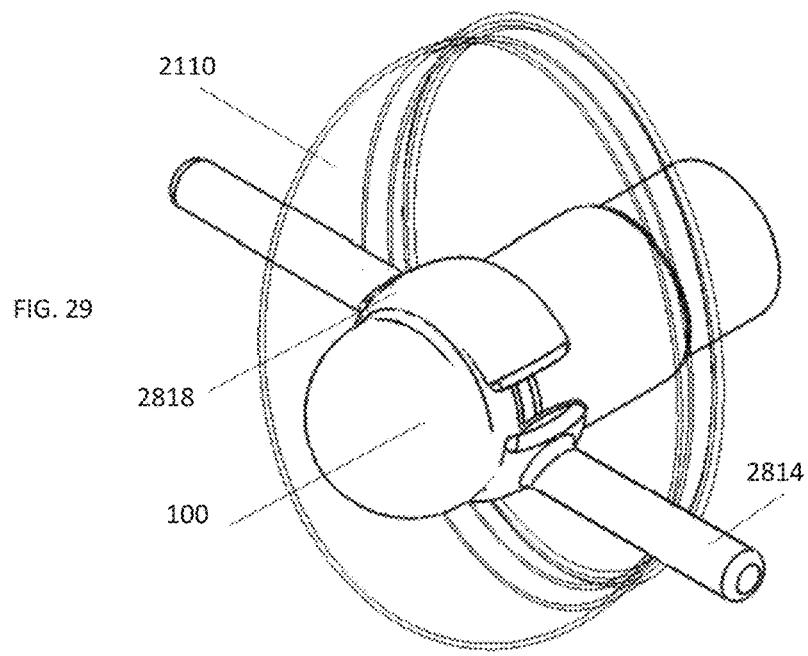

Yet another alternative arrangement of the foreskin retraction and inversion device 2800 is shown in FIGS. 28, 29, in combination with the accessor(ies) 2100, 2110. Here, the finger like projection contraption 2800 is shown to utilize two flexible arms 2810, each containing an extension element 2814 ending on one side with a respective arched element 2818 (which, as a pair are facing each other with concavities) while another side—the element 2814—being attached/fixed to the undergarment 2100/accessory 2110. Each of the arched elements 2818 can be thought of as a section of a ring, and the overall structure is dimensioned such as to accommodate and follow the change in the size and shape of the penis when such change occurs. The side of the arm 2810 containing the arched element 2818 may be made of soft material judiciously chosen to create a smooth contact with the penis 802. In operation, the two-arms are exerting pressure forces onto the penis 100 in two opposite directions (in reference to FIG. 29—along a vertical axis)) where the net of the two forces being negligible and substantially zero. The user pulls the foreskin towards the shaft to expose penis head (glans) 103, then places the arch-like projections 2818 on the opposite sides of the retracted and inverted foreskin against the glans 103 to use the glans 103 as anchoring location to maintain the arched elements 2818 (and, therefore, retracted and inverted foreskin underneath these elements) in substantially the same axial position along the shaft of the penis 100.

Figure 30:
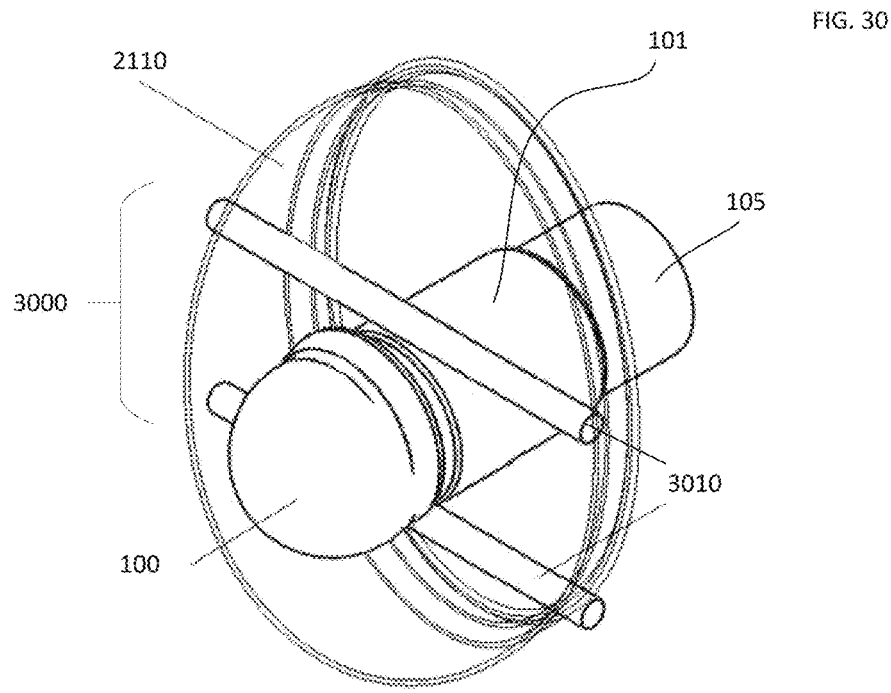
FIGS. 30, 31 illustrate the structure and use of another related embodiment of the invention.
Figure 31:
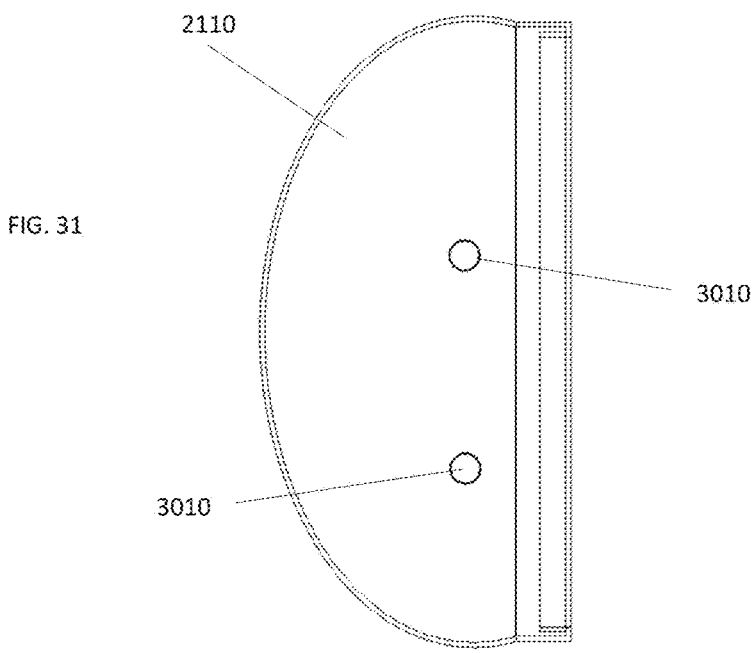

FIGS. 30, 31 aggregately provide illustrations to yet another related embodiment of the device 3000, that employs two rod-like or tube-like elements 3010 shown to cross the sagittal plane, FIG. 31, which in operation are to the undergarment (for example, passed through the openings in the supporting element 2110) at both ends. In operation, the elements 3010 tubes are disposed on and physically connected to the top and the bottom of the foreskin 101 to provide a reaction force needed for foreskin retraction and inversion as show in FIG. 30.

Yet in another related embodiment 3200, device may include a cylindrical ring 3210 supported by the arm-extensions 3214. Depending on the nature of the material used for the ring 3210, this embodiment may be configured to have the capability to stretch and constrict as needed to result in a desired pressure to hold the foreskin in the retracted position without interrupting blood circulation or causing discomfort while the device is worn with the ring 3210 inserted over the shaft of the penis and the arms 3214 supported in the undergarment 2110 (for example, in the openings of the protective element 2110). The design may consist of composite materials, both by combining homogeneous materials and using multiple materials heterogeneously in tandem, to satisfy the desired application. In operation—especially when the undergarment cup 2110 is made deformable, the user can push the sides of the cup to dilate the vertical distance between the arm extensions for the purpose of repositioning the shaft of the penis longitudinally.

FIGS. 35A, 35B, 35C illustrate a flexible sheet fastener 3500 (FIG. 35A: in a flat state; FIG. 35B: in a curved state) A flexible sheet fastener 3500 can be made of composite materials consisting of elastic or inelastic materials to maintain a desired pressure on the foreskin capable of changing shape to be wrapped around the penis to hold the retracted foreskin in place. The fastener 3500 can hold the position around the penis (around which the fastener is wrapped after the foreskin has been retracted, for example) using Velcro, stapler pin, or button, for example, as shown in FIG. 35C. Yet another related implementation 3600, schematically illustrated in FIGS. 36, 37, 38 and includes the center ring 3610 supported by the arm-extensions 3614 that are affixed in/supported by the components of the undergarment (for example, by the protective cup 2110 through the openings in which the arms 3614 are pulled and secured as a result of tension in/stretching of the arms 3614 formed due to contact of the protrusions 3614A with an outer surface of the protective cup 2110).

A skilled artisan will readily appreciate that substantially any of the embodiments illustrated in FIGS. 23, 28, 30, 36 can be operated, in contact with the shaft of the penis, at different distances from the body of the user—for example, be installed in substantial proximity of or in contact with the glans or away from the glans and closer to the body while securing the retracted and inverted foreskin. To vary the distance separating a chosen of these embodiments from the body of the user, a multiplicity of openings in the protective cup 2110 can be formed, and extensions arms such as 2310, 2814, and 3614 can be pulled through and secured in different pairs of such openings at different distances from the body of the user. As a result, any of these embodiment can be operated to perform at least three functions:—to retract foreskin backward to assist topical application of ointments for diseases such as balanitis, lichen sclerosis, etc. to eliminate the need for circumcision; to pull foreskin forward (when the ring portion of the embodiment is disposed above the non-inverted foreskin, for example) to alleviate phimosis—in this case the silicone ring (stopper) may be attached toward the front of the cup and the ring portion might attach differently to the foreskin, such as via clips; and even—act as a protector after circumcision to allow the wound to heal. Accordingly, the scope of invention also includes foreskin manipulation with the use of an embodiment of the device (such as one of these described above). The presence of the undergarment cup 2110 in at least some of the embodiments of the device may be additionally employed to prevent sexual use while device is being employed.

A person of ordinary skill in the art will readily appreciate that references throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. Accordingly—as the skilled artisan will readily appreciate—while in this specification the embodiments have been described in a way that enables a clear and concise specification to be written, it is intended that substantially none of the described embodiments can be employed only by itself to the exclusion of other embodiments (to the effect of practically restriction of some embodiments at the expense of other embodiments), and that substantially any of the described embodiments may be variously combined or separated to form different embodiments without parting from the scope of the invention. In particular, it will be appreciated that all features described herein at applicable to all aspects of the invention. For example, a combination of the features of the embodiments of substantially any of FIGS. 2, 4, 6, 10, 13, 15, 17, 19, 21, 23, 28, 30, 32, 35A, 36 with one another can be formed to generate an a related specific embodiment of the device of the invention for practical use, and each of those combinations remain within the scope of the invention as a given embodiment.

In addition, when the present disclosure describes features of the invention with reference to corresponding drawings (in which like numbers represent the same or similar elements, wherever possible), the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this particular detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Therefore, while generally the implementation of the invention is directed to a device for maintaining retraction and inversion of a foreskin of a male user (while keeping glans of an uncircumcised penis and mucosal membranes exposed), in which device includes a foreskin stopper unit dimensioned to be positioned onto and in contact with a shaft of the penis with the exposed glans and mucosal membranes against a neck of the glans, and in which device (1) the stopper unit is configured to press against the glans to form an anchoring feature for said stopper unit to create a reaction force for sustained inversion of the foreskin, and/or (2) the stopper unit is connected and affixed to a component of undergarment of the user, a specific embodiment of such device in which the stopper unit contains one or more of the following structural features—a) a tubular component containing at least one of a hollow cylindrical element and a hollow conical element a diameter of at least one of bases of which is dimensioned to anchor against the glans and a length to cover at least a portion of the inverted foreskin with the exposed mucosal membranes when installed over the shaft; b) a ring dimensioned to completely circumscribe the shaft at the neck of glans; c) a curved clip configured as a coil spring; d) multiple arched arms, each dimensioned to contact the shaft along a portion of a circumference thereof at the neck of glans while leaving a portion of said circumference exposed and not directly connected with one another; and e) multiple rods or tubes, each dimensioned to be installed in contact with and across the shaft at the neck of glans—is also a stand-alone related embodiment of the invention. Similarly, while the general scope of the method of maintaining a foreskin of a penis of a user in a retracted and inverted position (with a device that includes a foreskin stopper unit dimensioned to be positioned onto and in contact with a shaft of the penis with exposed glans and exposed mucosal membranes) is that including the actions of inverting the foreskin back to expose the glans and the mucosal membranes and disposing at least a first portion of the foreskin stopper unit at a shaft of the penis and over the inverted foreskin to hold the inverted foreskin in place (as a result of at least one of anchoring the device against at least one of glans of the penis and anchoring said stopper unit at an undergarment of the user), in at least one specific embodiment of the method the action of disposing may include one or more of the following steps: a) positioning a tubular component of the stopper unit over the shaft with an edge of the tubular component against the glans, wherein the tubular component contains at least one of a hollow cylindrical element and a hollow conical element a diameter of at least one of bases of which is dimensioned to anchor against the glans and a length to cover at least a portion of the inverted foreskin with the exposed mucosal membranes when installed over the shaft; b) locating a ring of the stopper unit over the shaft to completely circumscribe the shaft at the neck of glans; c) disposing a curved clip of the stopper unit onto the shaft; d) locating multiple arched arms of the stopper unit onto the shaft, each of the multiple arched arms dimensioned to contact the shaft along a portion of a circumference thereof at the neck of glans while leaving a portion of said circumference exposed and not directly connected with one another; and e) contacting each of multiple rods of the stopper unit with and across the shaft.

In operation, the initial retraction of the foreskin may be done by the operation of the device or the user himself who manually retracts and inverts the foreskin using his hands. The design may contact the circumference of the penis and foreskin to create desired pressure to ensure a fixed position of the device on the foreskin. To ensure foreskin retraction, the device requires a reaction force utilizing the glans of the penis, an undergarment, or a combination of both as an anchor for retraction. The topical cream or other medicine is applied on the affected area (in some cases—through perforations in the device) while the foreskin is kept retracted by this device.

The invention should not be viewed as being limited to the disclosed embodiment(s).

What is claimed is:

1. A device for maintaining retraction and inversion of a foreskin of a male user while keeping a glans of an uncircumcised penis and mucosal membranes exposed, the device comprising:
    a foreskin stopper unit comprising a tubular component dimensioned to be positioned onto and in contact with a shaft of the penis with the exposed glans and mucosal membranes, wherein
    i) said tubular component comprises mesh or multiple perforations through a wall thereof, through which, when the device is installed on the shaft, the exposed mucosal membranes remain in fluid communication with an environment surrounding the tubular component; and/or
    ii) said tubular component comprises first and second hollow cylinders each having different diameters and configured to be installed on the shaft co-axially and inside one another; and/or
    iii) said tubular component comprises an auxiliary hollow cylinder configured as a ring and an adjacent hollow cone having multiple perforations through a wall thereof, the auxiliary hollow cylinder being directly affixed to and extending from an edge of the hollow cone; and/or
    iv) said tubular component comprises a first hollow cylinder with a first wall and a first outer diameter, a second hollow cylinder having a second outer diameter and multiple perforations through a second wall thereof and a longitudinal slot extending along a portion of a length thereof, and a handle extending outwardly from the first hollow cylinder through the longitudinal slot and terminating at a radial distance exceeding the second diameter, and/or
    (v) wherein the foreskin stopper unit is connected and affixed to a component of an undergarment of the male user.

2. The device according to claim 1, wherein the foreskin stopper unit further includes at least one of:
    a) a ring dimensioned to completely circumscribe the shaft at the neck of the glans;
    b) a curved clip configured as a coil spring;
    c) multiple arched arms, each arched arm dimensioned to contact the shaft along a portion of a circumference thereof at the neck of the glans while leaving a portion of said circumference exposed, wherein the multiple arched arms are not directly connected with one another; and
    d) multiple rods, each rod dimensioned to be installed in contact with and across the shaft at the neck of the glans.

3. The device according to claim 2, wherein:
    the curved clip is affixed to the tubular component throughout openings in a wall of the tubular component; and/or
    the device comprises multiple radially-extending finger-like protrusions on an inner surface of at least one of the ring and the tubular component.

4. The device according to claim 1, wherein:
    the device comprises a curved clip configured as a coil spring and the curved clip is affixed to the tubular component throughout openings in a wall of the tubular component; and/or
    the device comprises multiple radially-extending finger-like protrusions on an inner surface of at least one of the ring and the tubular component.

5. The device according to claim 1, wherein the foreskin stopper unit includes an elastic material configured to maintain the shaft under radial pressure when in contact with the shaft.

6. A method of maintaining a foreskin of a penis of a user in a retracted and inverted position with a device according to claim 1, the method comprising:
    inverting the foreskin back to expose the glans and the mucosal membranes; and
    disposing at least a first portion of the foreskin stopper unit at the shaft of the penis and over the inverted foreskin to hold the inverted foreskin in place by anchoring the foreskin stopper unit against the glans of the penis and/or by anchoring said foreskin stopper unit at an undergarment of the user.

7. The method according to claim 6, wherein said step of disposing comprises at least one of:
    a) positioning the tubular component of the foreskin stopper unit over the shaft with an edge of the tubular component against the glans;
    b) placing a ring of the foreskin stopper unit over the shaft to completely circumscribe the shaft at the neck of the glans;
    c) disposing a curved clip of the foreskin stopper unit onto the shaft;
    d) locating multiple arched arms of the foreskin stopper unit onto the shaft, each of the multiple arched arms dimensioned to contact the shaft along a portion of a circumference thereof at the neck of the glans while leaving a portion of said circumference exposed; and e) contacting multiple rods of the foreskin stopper unit with and across the shaft.

8. The method according to claim 7, wherein the tubular component comprises a first hollow cylinder and a second hollow cylinder, the first hollow cylinder being inside the second hollow cylinder, and the method further comprising axially repositioning the first hollow cylinder of the tubular component within the second hollow cylinder of the tubular component by moving the handle that extends from the first hollow cylinder through the longitudinal slot in the second wall of the second hollow cylinder.

9. The method according to claim 6, further comprising maintaining radially-directed compression on the shaft caused by elasticity of the foreskin stopper unit disposed over the shaft or caused by an auxiliary component of the foreskin stopper unit affixing the foreskin stopper unit to the shaft.

10. The method according to claim 6, further comprising at least one of the following:

a) disposing a second portion of the foreskin stopper unit containing a first tubular section at the shaft prior to said inverting;

wherein said inverting includes inverting the foreskin over the second portion of the foreskin stopper that has been disposed over the shaft, and wherein said disposing the at least a first portion of the foreskin stopper unit includes disposing a second tubular section over the shaft of the penis and over the inverted foreskin;

b) securing at least one radial extension of the foreskin stopper unit in an opening formed in a protective cup of the undergarment;

c) retracting and inverting the foreskin manually prior to said disposing at least a first portion of the foreskin stopper unit;

d) retracting and inverting the foreskin as a result of application of the first portion of the foreskin stopper unit; and e) preventing sexual use of the shaft equipped as a result of encapsulation thereof in said protective cup.

11. A method for manipulation a foreskin of a penis of a user with a device according to claim 1, the method comprising:

with exposed glans and exposed mucosal membranes:

disposing at least a first portion of the foreskin stopper unit at the shaft of the penis and over the foreskin to hold the foreskin in place by anchoring the foreskin stopper unit against the glans of the penis and by anchoring said foreskin stopper unit at the component of the undergarment of the user, and changing a shape of the component of the undergarment of the user to reposition the at least a first portion of the foreskin stopper unit longitudinally with respect to the shaft to move the foreskin either over the glans and away from a body of the user or away from the glans and towards the body of the user to expose mucosal membranes.

* * * * *